United States Patent
Brown

(10) Patent No.: US 7,374,564 B2
(45) Date of Patent: May 20, 2008

(54) APPARATUS AND METHOD FOR CAUSING DEFLECTION OF A SURGICAL INSTRUMENT

(76) Inventor: Joe D. Brown, 8317 Front Beach Rd., Suite 21, Panama City Beach, FL (US) 32407

( * ) Notice: Subject to any disclaimer, the term of this patent is extended or adjusted under 35 U.S.C. 154(b) by 196 days.

(21) Appl. No.: 10/680,426

(22) Filed: Oct. 8, 2003

(65) Prior Publication Data

US 2004/0138678 A1    Jul. 15, 2004

Related U.S. Application Data

(60) Provisional application No. 60/416,588, filed on Oct. 8, 2002.

(51) Int. Cl.
*A61B 17/22* (2006.01)
(52) U.S. Cl. .......................... 606/127; 606/113; 606/114
(58) Field of Classification Search ................. 606/2.5, 606/13–17, 27, 110, 113, 114, 127; 600/101, 600/104, 1

See application file for complete search history.

(56) References Cited

U.S. PATENT DOCUMENTS

| | | | |
|---|---|---|---|
| 4,261,644 A | 4/1981 | Giannaris | |
| 4,503,569 A * | 3/1985 | Dotter | 623/1.19 |
| 4,930,494 A * | 6/1990 | Takehana et al. | 600/145 |
| 5,645,520 A * | 7/1997 | Nakamura et al. | 600/151 |
| 5,662,585 A * | 9/1997 | Willis et al. | 600/104 |
| 5,766,164 A | 6/1998 | Mueller et al. | |
| 5,944,701 A * | 8/1999 | Dubrul | 604/264 |
| 6,039,727 A | 3/2000 | Javier, Jr. et al. | |
| 6,066,131 A | 5/2000 | Mueller | |
| 6,077,298 A * | 6/2000 | Tu et al. | 623/1.19 |
| 6,110,164 A | 8/2000 | Vidlund | |
| 6,162,214 A | 12/2000 | Mueller et al. | |
| 6,224,612 B1 * | 5/2001 | Bates et al. | 606/114 |
| 6,240,231 B1 | 5/2001 | Ferrera et al. | |
| 6,344,037 B1 | 2/2002 | Suorsa et al. | |
| 6,458,076 B1 * | 10/2002 | Pruitt | 600/146 |
| 6,530,935 B2 * | 3/2003 | Wensel et al. | 606/159 |
| 6,702,846 B2 * | 3/2004 | Mikus et al. | 623/1.22 |
| 6,824,545 B2 * | 11/2004 | Sepetka et al. | 606/113 |
| 6,872,211 B2 * | 3/2005 | White et al. | 606/114 |
| 6,949,097 B2 * | 9/2005 | Stewart et al. | 606/41 |
| 6,966,906 B2 * | 11/2005 | Brown | 606/15 |
| 7,063,707 B2 * | 6/2006 | Bose et al. | 606/127 |

* cited by examiner

*Primary Examiner*—A. Farah
(74) *Attorney, Agent, or Firm*—Bacon & Thomas, PLLC

(57) ABSTRACT

An apparatus and method of precisely controlling deflection or twisting of a surgical instrument during surgery is applied to a surgical instrument incorporating a shape memory alloy. An example of such an instrument is a Nitinol urological retrieval coil. The shape memory alloy is caused to assume a predetermined shape when heated to a predetermined temperature not more than a few degrees above body temperature, by delivering irrigating fluid having a temperature above the transformation temperature of the shape memory alloy.

6 Claims, 1 Drawing Sheet

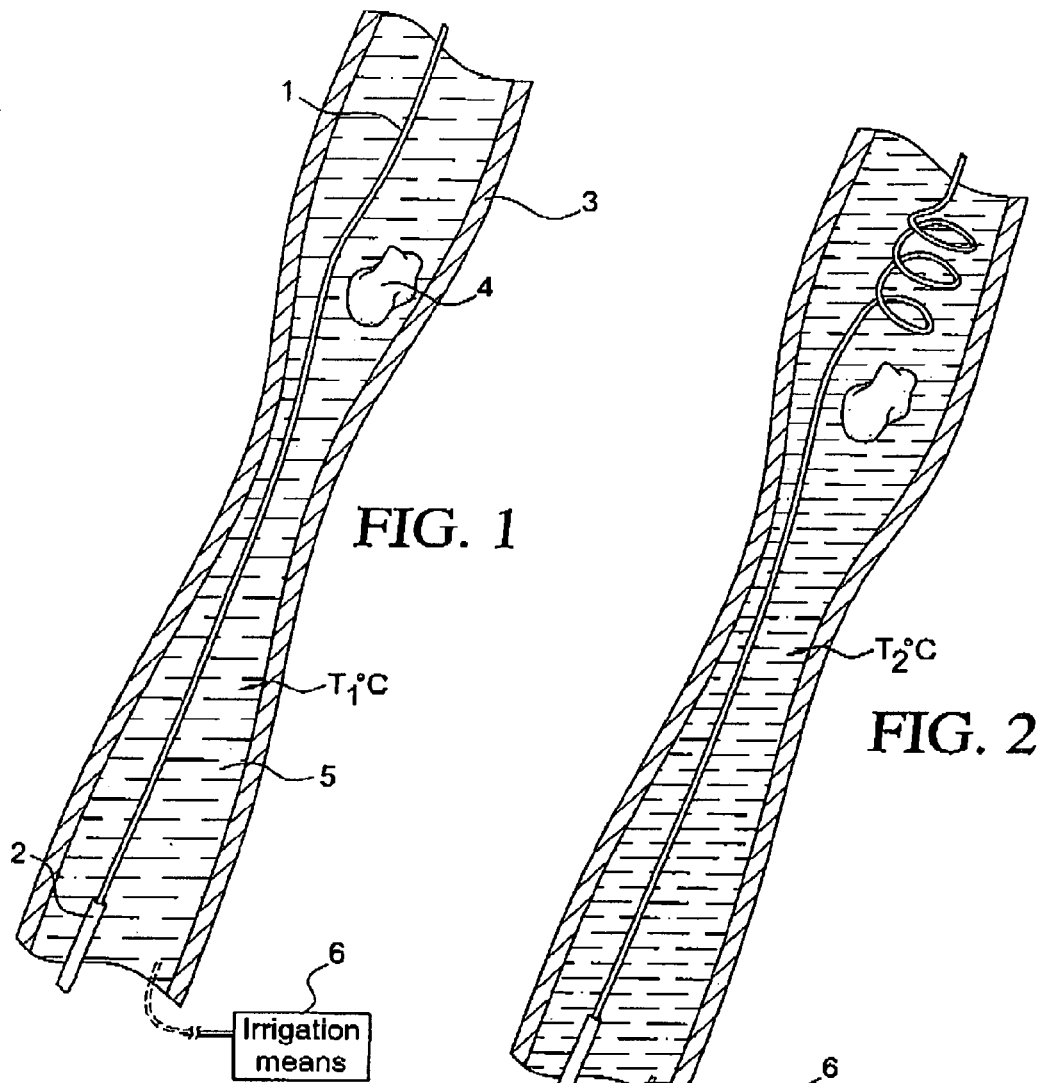

APPARATUS AND METHOD FOR CAUSING DEFLECTION OF A SURGICAL INSTRUMENT

This application claims the benefit of U.S. Provisional Application Ser. No. 60/416,588, filed Oct. 8, 2002.

BACKGROUND OF THE INVENTION

1. Field of the Invention

This invention relates to apparatus for deflecting a surgical instrument inserted into an endoscope, and to a method of causing the distal end of the surgical instrument to bend or twist during a surgical procedure.

2. Description of Related Art

U.S. Pat. No. 6,966,906, incorporated by reference herein, discloses apparatus for deflecting a surgical instrument inserted into an endoscope, and a method of causing the surgical instrument to deflect during a surgical procedure, in which the surgical instrument is provided with a sheath made of a shape memory alloy having an austinitic transformation temperature no more than a few degrees above the normal temperature of the human body, and in which transformation to a desired shape is caused to occur by increasing the temperature of an irrigation fluid to just beyond the transformation temperature of the instrument.

SUMMARY OF THE INVENTION

The present application extends the principle of using an irrigation fluid to cause transformation of a shape memory alloy to surgical applications other than those involving an endoscope tube and instruments of the type disclosed in U.S. Pat. No. 6,966,906.

An example of an instrument to which the principles of the invention may be applied is the Stone Cone™ Nitinol Urological Retrieval Coil marketed by Boston Scientific Corporation. The Stone Cone™ coil is a Nitinol coil which, when extended out of a sheath and past a stone, twists into a coil so as to trap or retrieve the stone.

The present invention provides a way to precisely control twisting of the coil, or in general to control deflection or twisting of a surgical instrument during surgery, whether or not used within an endoscope. It applies to any surgical instrument incorporating a shape memory alloy that causes the surgical instrument to assume a predetermined shape when heated to a predetermined temperature not more than a few degrees above body temperature, and involves causing the transformation by delivering irrigating fluid having a temperature above the transformation temperature of the shape memory alloy.

BRIEF DESCRIPTION OF THE DRAWINGS

FIG. 1 is a cross-sectional side view of a surgical instrument before undergoing shape-transformation during a urinary tract surgical procedure, according to the principles of a preferred embodiment of the invention.

FIG. 2 is a cross-sectional side view of the surgical of FIG. 1, after shape-transformation.

FIG. 3 is a flowchart illustrating a method for using the apparatus of FIG. 1.

DETAILED DESCRIPTION OF THE PREFERRED EMBODIMENTS

As shown in FIG. 1, a surgical instrument 1 made, in part, of a shape memory alloy, is inserted through a sheath 2 into a passage 3 such as the urinary tract of a patient suffering from a stone 4. Irrigation fluid 5 having a temperature $T_1$ is typical provided through a means 6.

The surgical instrument can be any instrument made of a shape memory alloy that deflects or twists at an austinitic transformation temperature $T_T$ that is above temperature $T_1$, but that is not so warm that it would cause damage to the patient or interfere with the surgical procedure. For example, the surgical instrument may be a urological retrieval coil similar to the Stone Cone™ mentioned above, which is essentially a coated Nitinol wire arranged to twist into a coil when extended from its sheath.

Alternatively, the surgical instrument may be any instrument having at least a portion composed of a shape memory alloy, including but not limited to Nitinol, and arranged to deflect or twist into a predetermined shape at is a temperature not more than a few degrees above a temperature of a body, whether animal or human, into which it is inserted.

In addition, the surgical instrument may be arranged to permit it to be retracted from a location within a patient by first reducing the temperature of the shape memory alloy to some value below its martinsitic transition temperature.

The apparatus of the invention includes the surgical instrument, and any means 6 for delivering irrigation fluid having a temperature above the transformation temperature of the shape memory alloy. The irrigation fluid may be, but is not limited to, water or other aqueous solutions.

As illustrated in FIG. 3, the method of the invention involves inserting a surgical instrument of the above-described type to a location at which shape transformation is desired (step 1). The surgical instrument is then exposed to irrigation fluid having a temperature $T_2$ above the transformation temperature $T_T$ of the shape memory alloy. In the case of a urological retrieval coil, the shape memory alloy transforms into a coil that can be used to retrieve or trap stones in association with an intracorporeal lithotripter procedure. As is well-known, the coil or other shape is determined during manufacture of the instrument by forming the alloy into the desired shape at high temperature, and subsequently cooling and deforming the alloy as it cools.

Having thus described a preferred embodiment of the invention in sufficient detail to enable those skilled in the art to make and use the invention, it will nevertheless be appreciated that numerous variations and modifications of the illustrated embodiment may be made without departing from the spirit of the invention, and it is intended that the invention not be limited by the above description or accompanying drawings, but that it be defined solely in accordance with the appended claims.

I claim:

1. A surgical instrument, comprising:
   a member made of a shape memory alloy arranged to be inserted into a patient,
   wherein when irrigation fluid having a temperature several degrees higher than a body temperature of said patient but not high enough to cause harm to a patent is caused to flow past said member, following insertion of the member into the patient, the member assumes a predetermined shape to perform a surgical function, and
   wherein the shape assumed by the member is a coil shape, the member thereby serving as a urological retrieval coil.

2. The surgical instrument of claim 1, wherein a distal end of the surgical instrument is caused to bend and/or twist into said coil shape when the temperature of the shape memory alloy is increased above its austinitic transition temperature.

3. The surgical instrument of claim 2, wherein the austinitic transition temperature of the shape memory alloy is adjusted to be several degrees above the typical temperature of a human body (98.6 degrees F.).

4. A surgical method, comprising the steps of inserting a surgical instrument made of a shape memory alloy into a patient; and causing the surgical instrument to assume a predetermined shape by causing irrigation fluid having a temperature several degrees higher than a body temperature of the patient but not high enough to cause harm to the patient to flow past the instrument following insertion of the surgical instrument into the patient, wherein the shape assumed by the member is a coil shape, the member thereby serving as a urological retrieval coil.

5. The surgical method of claim 4, wherein a distal end of the surgical instrument is caused to bend and/or twist into said coil shape when the temperature of the shape memory alloy is increased above its austinitic transition temperature.

6. The surgical method of claim 5, wherein the austinitic transition temperature of the shape memory alloy is adjusted to be several degrees above the typical temperature of a human body (98.6 degrees F.).

* * * * *